United States Patent
Kaufmann et al.

(10) Patent No.: US 9,192,714 B2
(45) Date of Patent: Nov. 24, 2015

(54) CARRIER FOR AN INFUSION SYSTEM

(75) Inventors: Heiner Kaufmann, Bern (CH); Gerald Studer, Flaach (CH)

(73) Assignee: Roche Diabetes Care, Inc., Indianapolis, IN (US)

(*) Notice: Subject to any disclaimer, the term of this patent is extended or adjusted under 35 U.S.C. 154(b) by 258 days.

(21) Appl. No.: 12/757,326

(22) Filed: Apr. 9, 2010

(65) Prior Publication Data
US 2010/0234805 A1  Sep. 16, 2010

Related U.S. Application Data

(63) Continuation of application No. PCT/EP2008/008573, filed on Oct. 10, 2008.

(60) Provisional application No. 60/979,272, filed on Oct. 11, 2007, provisional application No. 60/979,279, filed on Oct. 11, 2007.

(51) Int. Cl.
*A61M 5/142* (2006.01)
*A45F 5/00* (2006.01)

(52) U.S. Cl.
CPC ...... *A61M 5/14248* (2013.01); *A45F 2005/008* (2013.01); *A61M 5/14244* (2013.01); *A61M 2005/14268* (2013.01); *A61M 2209/088* (2013.01)

(58) Field of Classification Search
CPC .......... A61M 5/14248; A61M 5/14244; A61M 2005/14268; A61M 2005/14252; A61M 2209/088; A61B 5/683–5/6833; A45F 2005/008
USPC .......................................... 604/174, 151–155
See application file for complete search history.

(56) References Cited

U.S. PATENT DOCUMENTS

| | | | |
|---|---|---|---|
| 6,558,351 B1* | 5/2003 | Steil et al. | 604/131 |
| 6,659,978 B1 | 12/2003 | Kasuga et al. | |
| 6,948,918 B2* | 9/2005 | Hansen | 417/395 |
| 2001/0056262 A1 | 12/2001 | Cabiri et al. | |
| 2003/0106917 A1 | 6/2003 | Shelter et al. | |
| 2006/0036214 A1* | 2/2006 | Mogensen et al. | 604/164.01 |
| 2006/0177351 A1* | 8/2006 | Heiniger et al. | 422/100 |
| 2006/0264835 A1* | 11/2006 | Nielsen et al. | 604/174 |
| 2009/0221971 A1* | 9/2009 | Mejlhede et al. | 604/180 |

FOREIGN PATENT DOCUMENTS

| | | |
|---|---|---|
| EP | 1 338 295 A1 | 8/2003 |
| EP | 1 754 890 A2 | 2/2007 |
| FR | 2 734 162 | 11/1996 |
| WO | 96/37244 | 11/1996 |
| WO | 2007/035666 A2 | 3/2007 |
| WO | 2007/065944 A1 | 6/2007 |
| WO | 2007/071255 A1 | 6/2007 |
| WO | WO 2007071255 A1 * | 6/2007 |

OTHER PUBLICATIONS

International Search Report, Appln. No. PCT/EP2008/008573, Applicant Roche Diagnostics GmbH, Apr. 28, 2009, 8 pages.

* cited by examiner

*Primary Examiner* — Quynh-Nhu H Vu
*Assistant Examiner* — Jenna Zhang
(74) *Attorney, Agent, or Firm* — Dinsmore & Shohl LLP

(57) ABSTRACT

Infusion systems for holding an infusion pump on the body of a user are provided. According to one embodiment, the infusion system includes: a carrier frame; a guiding member disposed on the carrier frame; and a linear guide on the infusion pump wherein, when the infusion pump is attached to the carrier frame, the guiding member and the linear guide mate with each other to hold the infusion pump in place.

14 Claims, 17 Drawing Sheets

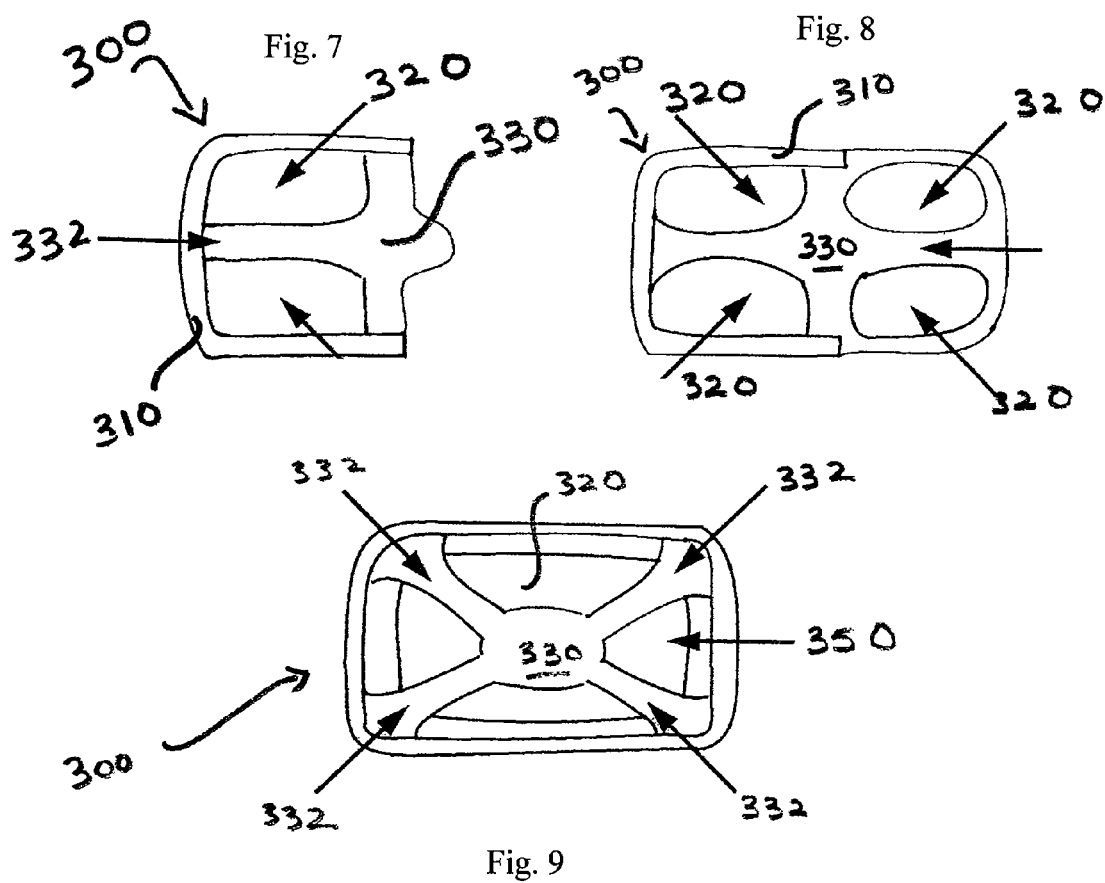

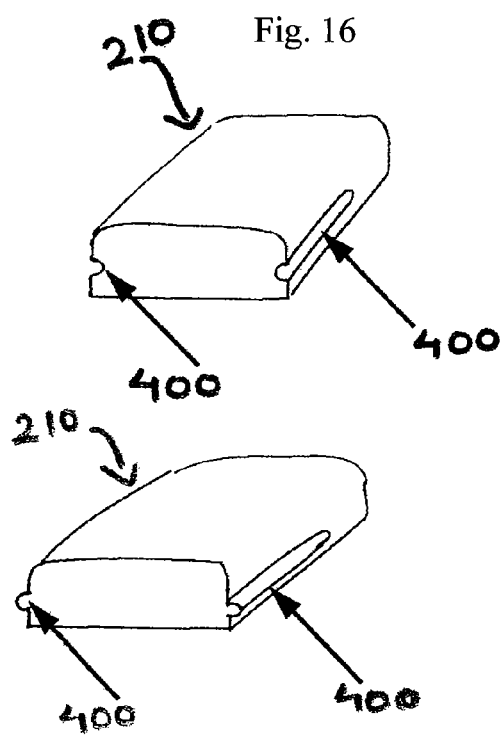
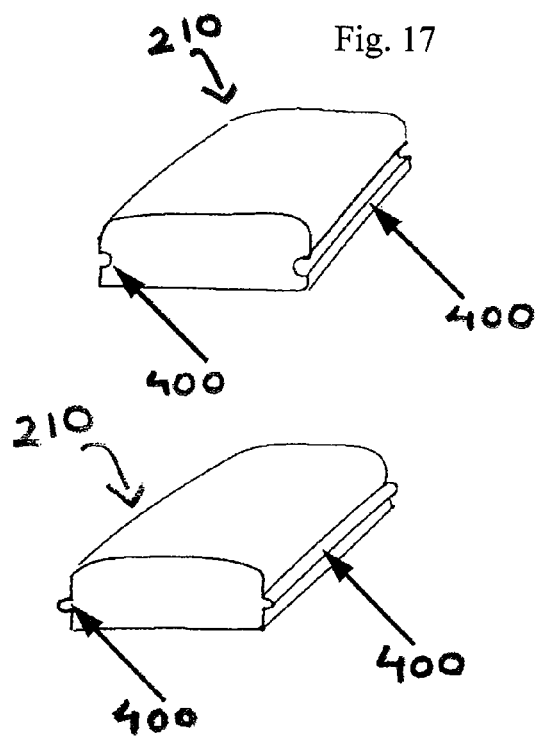
Fig. 16  Fig. 17
Fig. 18  Fig. 19

Fig. 35
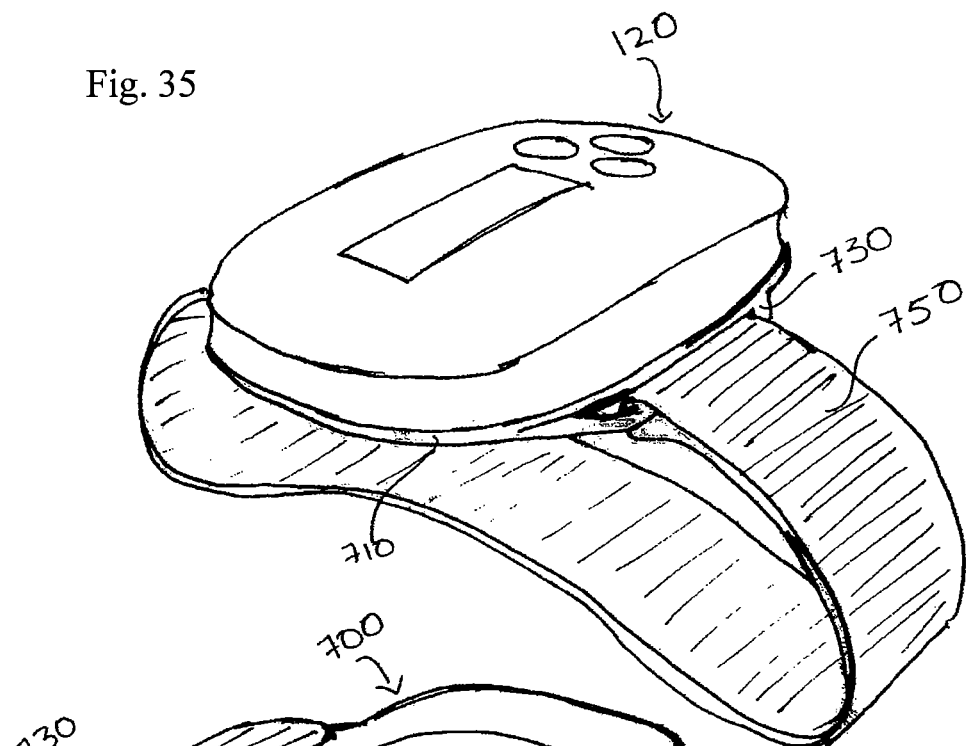
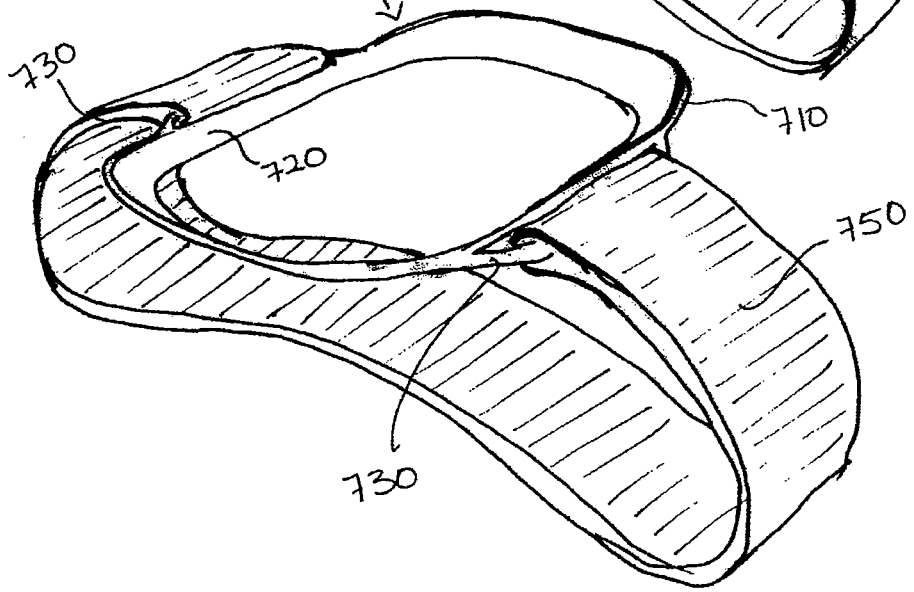
Fig. 36

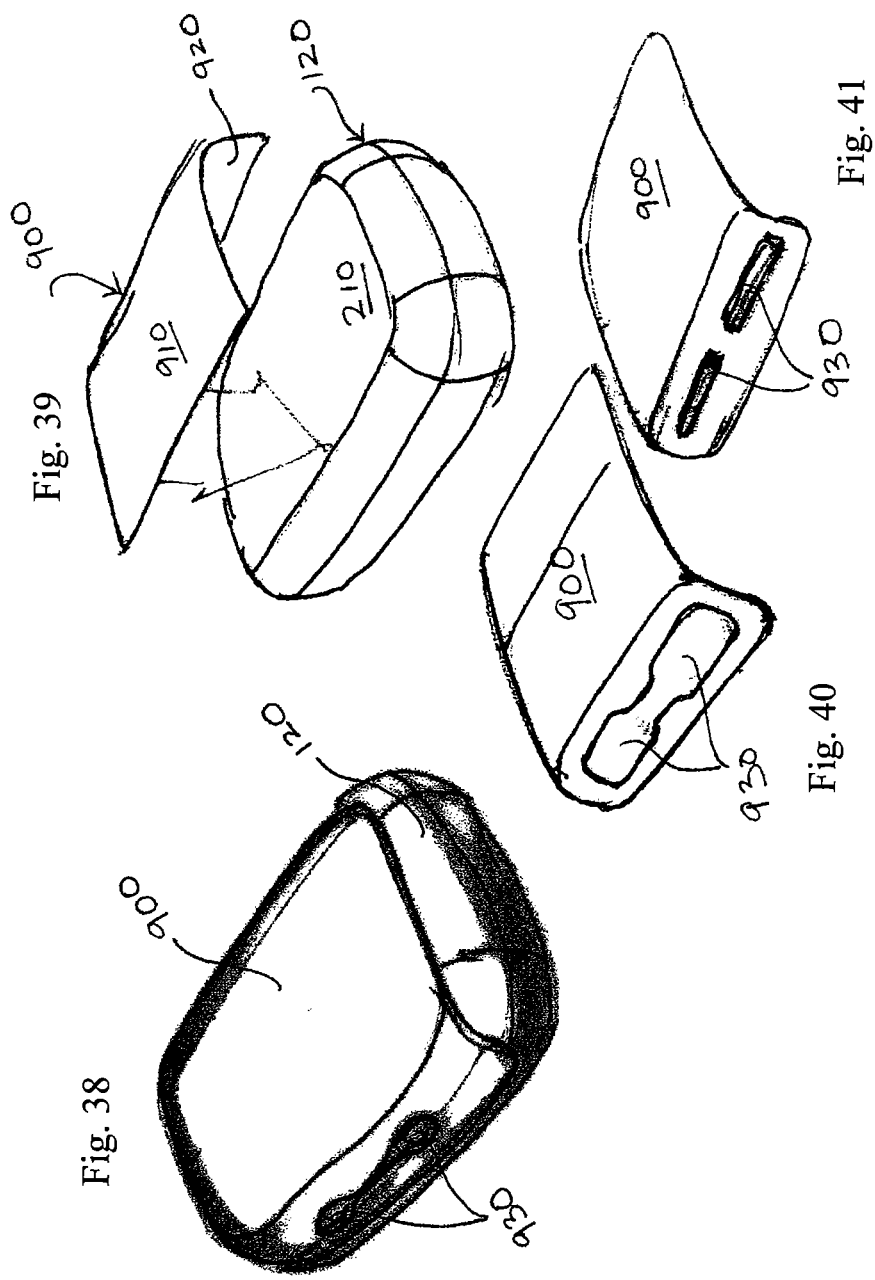

CARRIER FOR AN INFUSION SYSTEM

CROSS REFERENCE TO RELATED APPLICATIONS

This application is a continuation of International Application No. PCT/EP2008/008573 filed Oct. 10, 2008 which claims priority to U.S. Provisional Application No. 60/979,272 and U.S. Provisional Application No. 60/979,279, both filed on Oct. 11, 2007, the disclosures of which are incorporated herein by reference.

TECHNICAL FIELD

The embodiments described herein relate to systems for attaching a medical device to human body. Specifically it relates to carriers for infusion systems.

BACKGROUND

Medical devices that pump medication into an individual are known and commonly used in the medical industry. Typically, the medication that is delivered from such medical devices, or infusion systems, depends on the medical condition that is sought to be treated. For example, it is common to deliver insulin using an insulin pump to treat a diabetic patient.

Typically, the infusion systems include a reservoir or a cartridge that contains the medication. Due to trend towards the miniaturization of products, there is an expectation that the infusion systems be small and wearable for discrete operation. Since different users typically wear the infusion system in different places, it is desirable to provide an interface that will allow a user this flexibility. As the size of the infusion system becomes smaller, the infusion system may be attached directly to the skin of the user. In many cases, the medication is infused by adhering the infusion system to the stomach area. Human skin is flexible and pliable. In many cases the stomach area often comprises skin folds. The application of carriers between such skin folds may cause discomfort. Additionally, the skin tends to stretch-out more in the vertical axis than in the horizontal axis. Large pressure sensitive adhesives in the vertical axis may inhibit skin movement and induce stress. Also, the pressure sensitive adhesive may be difficult for the user to access. Furthermore, when carriers are worn on the skin, perspiration (skin breathing) is reduced and may lead to skin irritation.

Therefore, a needs exists for carriers where the infusion system can be comfortably worn on the skin without hindering the operation of the infusion system.

SUMMARY

It is against the above background that the present disclosure is provided.

According to one embodiment, an infusion system for holding an infusion pump on the body of a user is provided. The system includes: a carrier frame; a guiding member disposed on the carrier frame; and a linear guide on the infusion pump wherein, when the infusion pump is attached to the carrier frame, the guiding member and the linear guide mate with each other to hold the infusion pump in place.

In another embodiment, a method of carrying an infusion pump on a human body is provided. The method includes: providing a carrier having a carrier frame wherein the carrier holds the infusion pump; providing a guiding member on the carrier frame; providing a linear guide on the infusion pump; and bringing the carrier and the infusion pump into contact such that the guiding member and the linear guide mate with each other.

In yet another embodiment, an infusion system for holding an infusion pump on the body of a user is provided. The system includes: a carrier frame; a first attaching means on the carrier frame; and a second attaching means on the infusion pump wherein, when the infusion pump is attached to the carrier frame, the first attaching means and the second attaching means mate with each other to hold the infusion pump in place.

These and other features and advantages of the present disclosure will be more fully understood from the following detailed description taken together with the accompanying claims.

BRIEF DESCRIPTION OF THE DRAWINGS

The following detailed description of the embodiments of the present invention can be best understood when read in conjunction with the following drawings, where like structure is indicated with like reference numerals and in which:

FIG. 7 depicts a top plan view of a carrier frame with two cut-offs according to one or more of the embodiments shown and described herein;

FIG. 8 depicts a top plan view of a carrier frame with four cut-offs according to one or more of the embodiments shown and described herein;

FIG. 9 depicts a top plan view of a carrier with four cut-offs and connection bars to the edges according to one or more of the embodiments shown and described herein;

FIG. 16 depicts a perspective view of a drug delivery device with concave linear according to one or more of the embodiments shown and described herein;

FIG. 17 depicts a perspective view of a drug delivery device with concave linear according to one or more of the embodiments shown and described herein;

FIG. 18 depicts a perspective view of a drug delivery device with convex linear according to one or more of the embodiments shown and described herein;

FIG. 19 depicts a perspective view of a drug delivery device with convex linear according to one or more of the embodiments shown and described herein;

FIG. 35 depicts a perspective view of an infusion pump attached to a carrier according to one or more of the embodiments shown and described herein;

FIG. 36 depicts a perspective view of the carrier with an attached wrist band according to one or more of the embodiments shown and described herein;

FIG. 38 depicts a top view of a carrier attached to an infusion pump as a top clip on according to one or more of the embodiments shown and described herein;

FIG. 39 depicts a top view of a carrier attached to an infusion pump as a top clip on according to one or more of the embodiments shown and described herein;

FIG. 40 depicts a top view of a carrier attached to an infusion pump as a top clip on according to one or more of the embodiments shown and described herein;

FIG. 41 depicts a top view of a carrier attached to an infusion pump as a top clip on according to one or more of the embodiments shown and described herein;

DETAILED DESCRIPTION

Carriers for carrying infusion systems or for attaching infusion systems to human skin are described herein. Infusion systems may be attached to the skin of a user by the carriers and concealed from view. In embodiments of the present disclosure, the carriers provide wearing comfort and accessibility for handling by the user. The carriers may successfully adhere a rigid device with a heightened center of gravity above the adhesion level to flexible and pliable skin for prolonged periods of time. The carriers are capable of reducing the stress and shear forces applied to the skin in order to reduce the chance of detachment from the skin, and wearing discomfort. Carriers for providing wearing comfort and handling during the application, use and removal of infusion systems to skin will be described in greater detail hereinafter.

The present disclosure describes carriers for the attachment of infusion systems to skin. The attachment provides the user with access for handling and wearing comfort. Embodiments of the carrier are disposed between a drug delivery device and human skin such that the device is reliably attached to the skin, and may remain so for an extended period of time.

Figure 1:
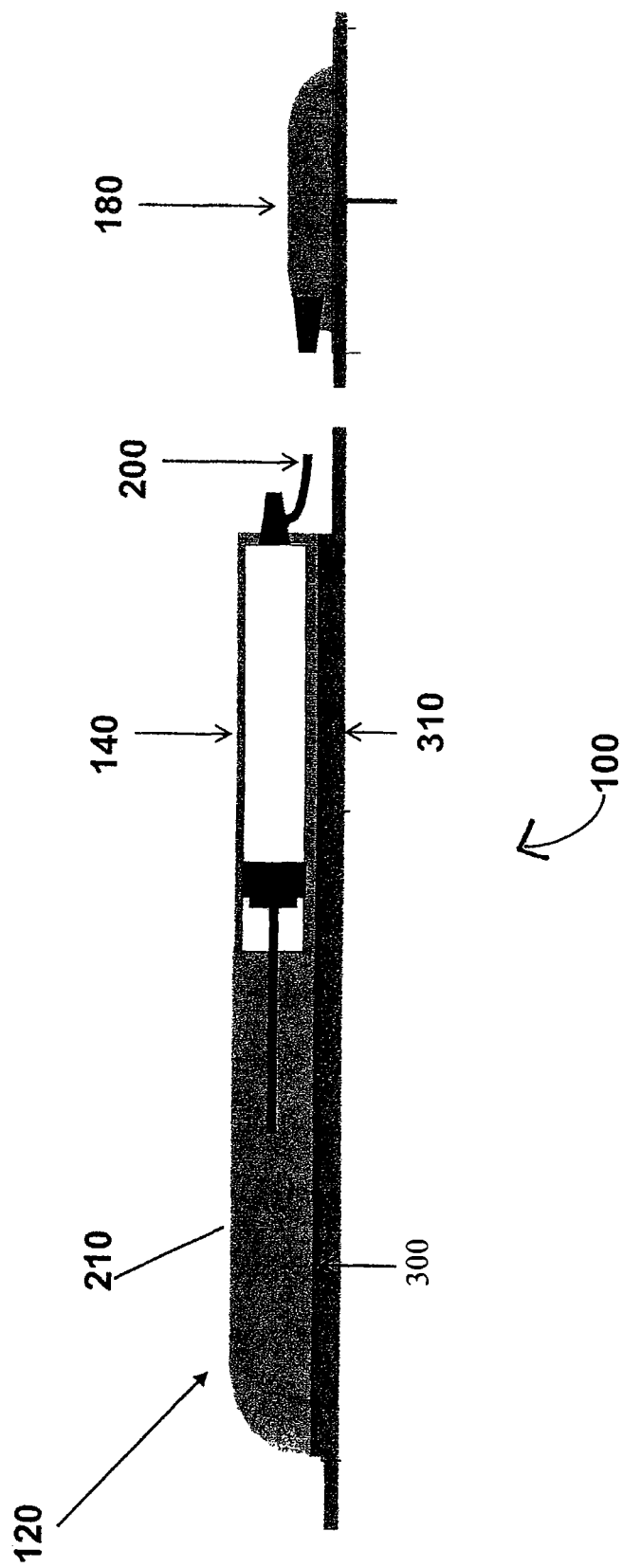
FIG. 1 depicts a perspective view of an infusion delivery system according to one or more of the embodiments shown and described herein.
Figure 2:
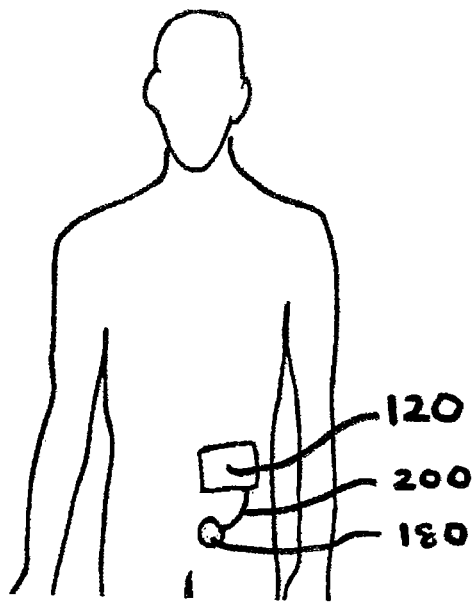
FIG. 2 depicts a frontal view of a human body with attached drug delivery device in horizontal axis according to one or more of the embodiments shown and described herein.

Referring to FIGS. 1 and 2, in embodiments of the present disclosure an infusion system 100 comprises an infusion pump 120, a fluid storing member 140, and an infusion set (not completely shown) 180 that is connected to the fluid storing member 140 through a tube 200. The infusion system 100 is depicted in the drawings as an insulin pump within insulin in the fluid storing member 140. Although an insulin pump is shown, it is noted that infusion systems 100 of the present disclosure are not limited to insulin pumps, and may be any pump capable of delivering medication to a user.

Although not depicted in the figures, embodiments of the infusion pump 120 comprise at least one control that controls the infusion of medication from fluid storing member 140. In another embodiment, the infusion pump 120 comprises a display. Additionally, it is noted that the infusion pump 120 may be controlled remotely to dispense medication using a remote control device such as, for example, a smart phone, a PDA, mobile device, and the like. Furthermore, the infusion pump 120 may be a one time use pump that is disposed after the medication is fully dispensed by the pump.

Referring again to FIG. 1, embodiments of infusion system 100 comprise an infusion pump 120 comprising an infusion pump housing 210. The infusion pump housing 210 houses a drive unit for dispensing the medication from the fluid storing member 140 to the user through the infusion set 180. In another embodiment, the infusion system 100 comprises a carrier 300 that attaches the infusion pump 120 to the body of a user. While, the carrier 300 is depicted as a device for attaching an infusion pump 120 to the skin of a user, it is noted that the carrier 300 can be adapted to hold a small infusion pump 120 without being attached to the skin of a user.

Figure 3:
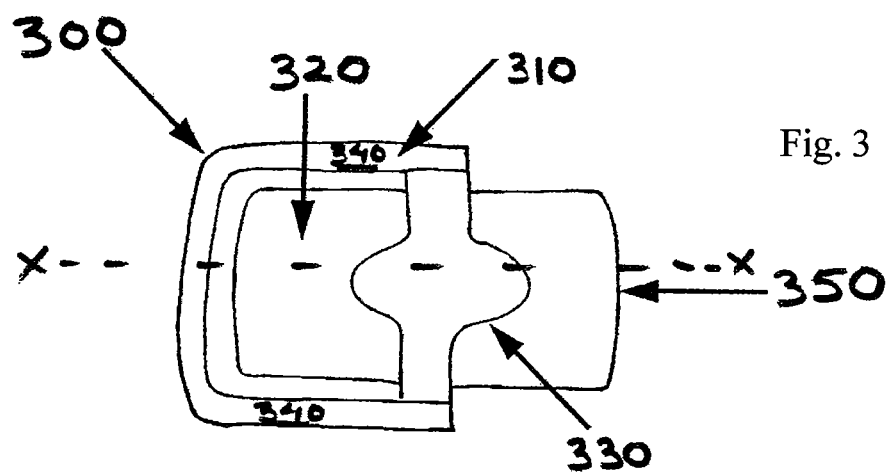
FIG. 3 depicts a top plan view of a carrier with small pressure sensitive adhesive according to one or more of the embodiments shown and described herein.

In an embodiment of the present disclosure, as depicted in FIGS. 1-3, the infusion pump housing 210 is removably attached to the carrier 300, and disposed on the top of the carrier 300. The bottom of the carrier 300 comprises an adhesive layer 350, such as, for example plaster. The carrier 300 is removably attached to the skin of the user via the adhesive layer 350. For example, the user can attach the carrier 300 with the adhesive layer 350 onto the user's skin and then attach the infusion pump 120 to the carrier. Alternatively, the user may attach the infusion pump 120 to the carrier 300 and then attach the carrier 300 to the skin. Although the infusion pump 120 and carrier 300 (not shown in FIG. 2) are depicted as being attached about the abdomen of the user, it is noted that the infusion system 100 may be worn anywhere on the body, such as, but not limited to the back. For the purpose of defining and describing the present disclosure, the term "top," as used herein, means the portion of the carrier 300 that the infusion pump 120 attaches to, and the term "bottom," as used herein, means the portion of the carrier 300 that attaches to the skin of a user.

Referring now to FIGS. 3, 4, 7-10, 12, and 14, embodiments of the carrier 300 comprise a carrier frame 310. The carrier frame 310 is manufactured using a rigid material such as plastic. In further embodiments, the carrier frame 310 is manufactured from a flexible or soft material such as, for example, textile. In still further embodiments, the carrier frame 310 comprises one or more cut-offs 320. The one or more cut-offs 320 are at least partially surrounded by the carrier frame 310, and are defined by an area that has been cut off of the carrier frame 310.

Referring now to FIGS. 1, 3, 4, 6, and 9-15, embodiments of the carrier 300 comprise an adhesive layer 350 disposed on the bottom of the carrier 300. The adhesive layer 350 is a pressure sensitive adhesive such that upon application of pressure to the adhesive layer 350, the carrier 300 attaches to the skin of the user. Pressure sensitive adhesives may comprise silicone, butyl or acrylic components that are formulated in such a way so that they adhere to the skin. In other embodiments, the adhesive layer 350 does not extend to the edges of the carrier 300 in the vertical axis. When the adhesive layer 350 is attached to the user, the skin of the user can be naturally stretched-out in the vertical axis during body movements. Good wearing comfort is achieved by the naturally stretched and low stress skin.

In another embodiment of the present disclosure, depicted in FIG. 3, the carrier 300 comprises an attachment area 330. The attachment area 330 attaches the carrier frame 310 to the adhesive layer 350. The attachment area is disposed along the horizontal axis X-X, and defines a central region on the carrier frame 310. The carrier 300 rotates freely about the horizontal axis, and provides flexibility for the use of the infusion pump 120.

Referring still to FIG. 3, further embodiments of the carrier frame 310 comprise a guiding member 340. The guiding member 340 secures the infusion pump 120 to the carrier 300. In one embodiment, the guiding member 340 is a ramp that mates with the infusion pump housing 210 to hold the infusion pump 120 in the carrier 300. In another embodiment, the guiding member 340 is an indentation that secures the infusion pump 120 to the carrier 300 after the infusion pump 120 is slid into the carrier 300.

Figure 5:
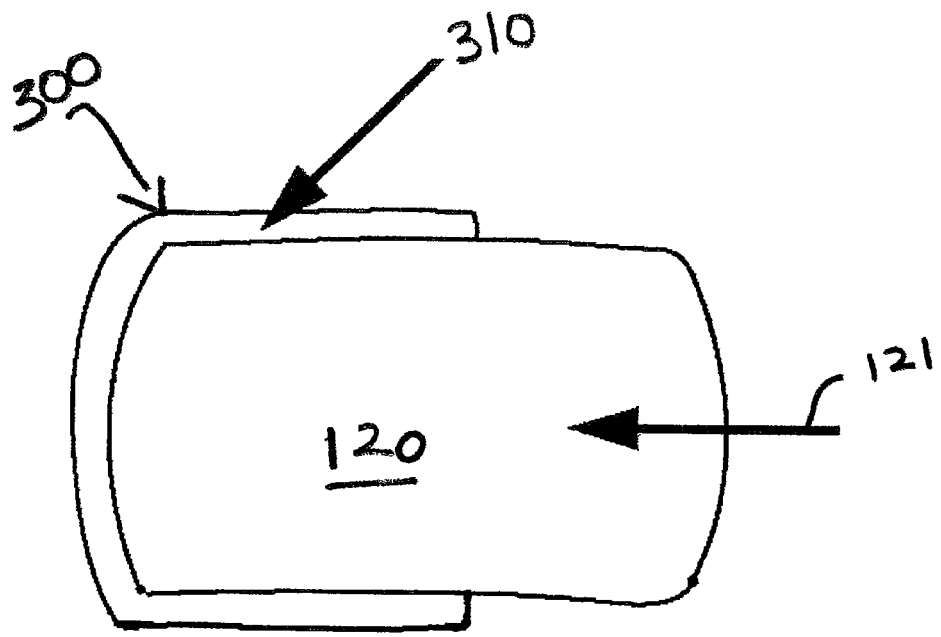
FIG. 5 depicts a top plan view of an attached infusion delivery system according to one or more of the embodiments shown and described herein

Referring now to FIGS. 3 and 5, an infusion pump 120 is attached to the carrier 300 according to an embodiment of the present disclosure. The adhesive layer 350 is covered by the infusion pump 120 after it is attached to the carrier 300. For example, the infusion pump 120 is attached to the carrier 300 by pushing the infusion pump 120 along the attaching direction 121. Once pushed into place, the infusion pump 120 obscures the adhesive layer 350 from view.

Figure 4:
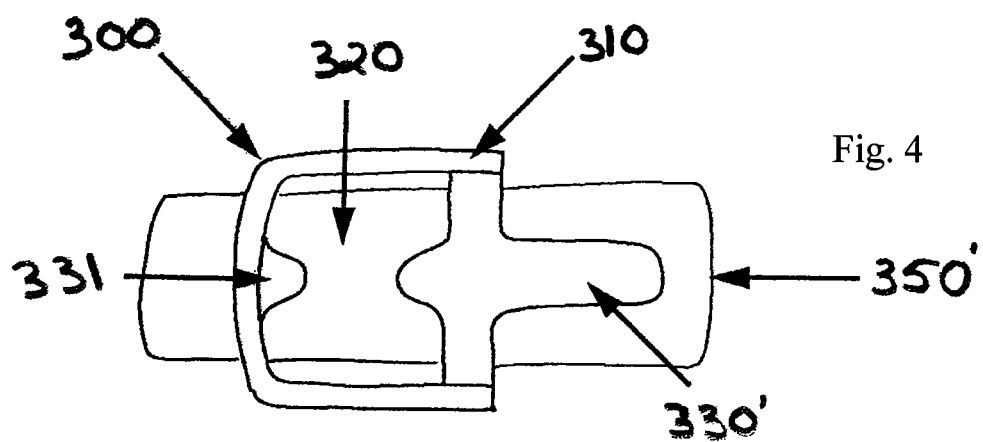
FIG. 4 depicts a top plan view of a carrier with large pressure sensitive adhesive according to one or more of the embodiments shown and described herein.
Figure 6:
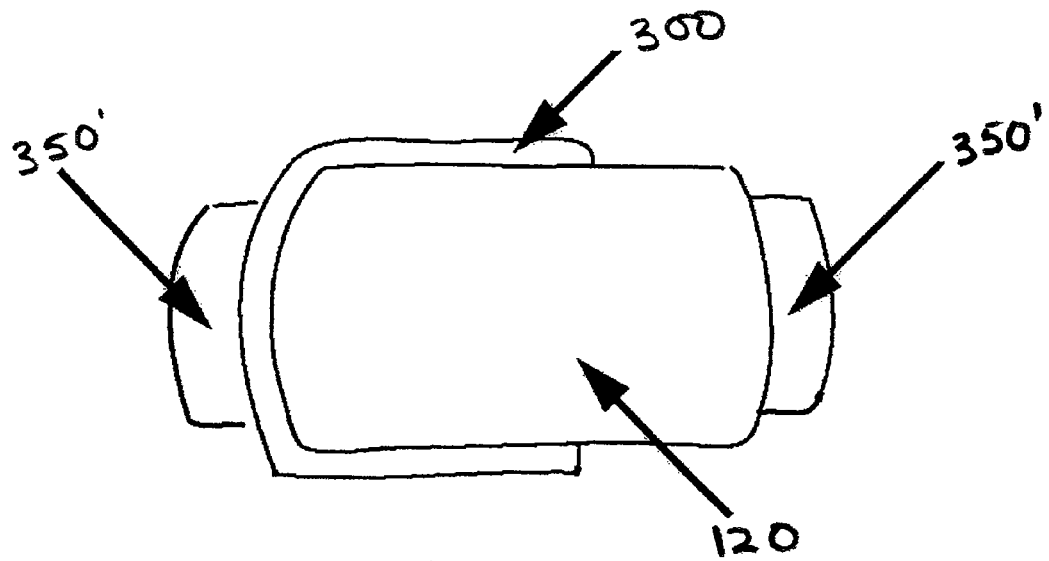
FIG. 6 depicts a top plan view of an attached drug delivery system according to one or more of the embodiments shown and described herein.
Figure 10:
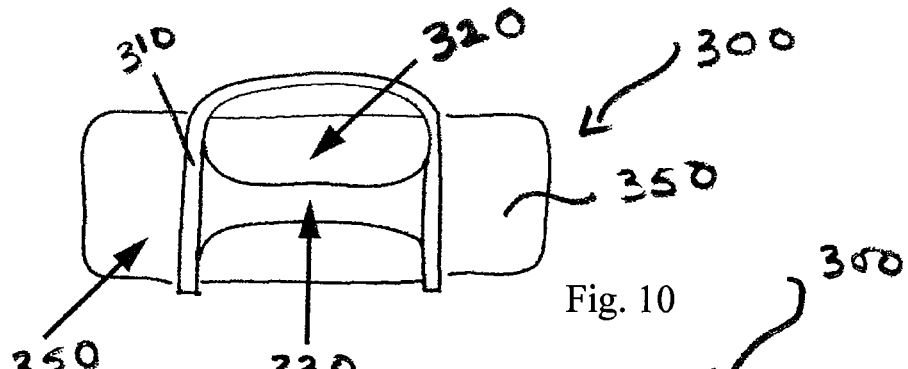
FIG. 10 depicts a top plan view of a carrier for attaching the drug delivery system in a vertical position according to one or more of the embodiments shown and described herein.
Figure 11:
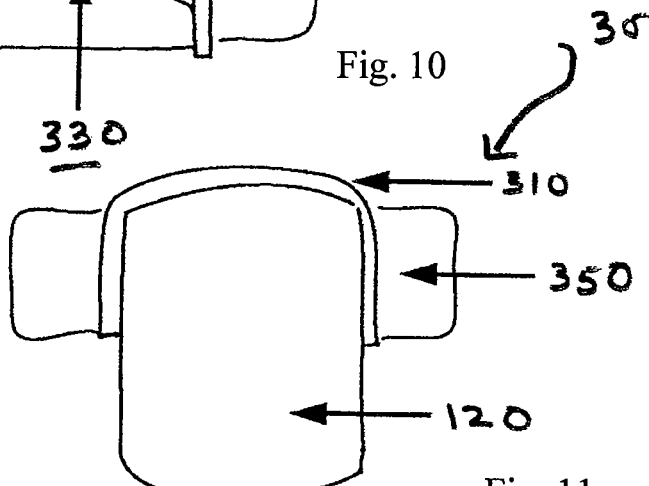
FIG. 11 depicts a top plan view of an attached drug delivery system in a vertical position according to one or more of the embodiments shown and described herein.
Figure 12:
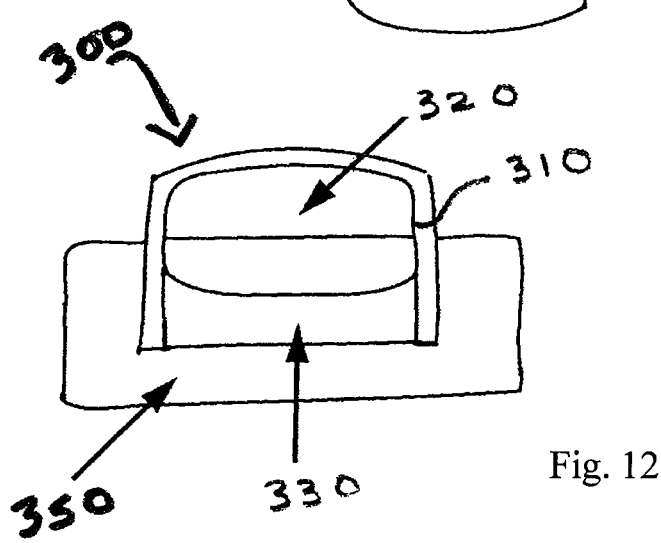
FIG. 12 depicts a top plan view of a carrier for attaching the drug delivery system in a vertical position according to one or more of the embodiments shown and described herein.
Figure 13:
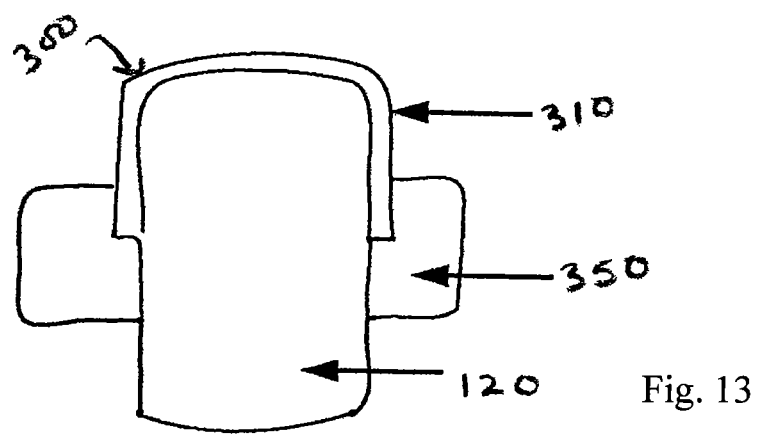
FIG. 13 depicts a top plan view of an attached drug delivery system in a vertical position according to one or more of the embodiments shown and described herein.

FIGS. 4 and 6 depict further embodiments of the carrier 300. The carrier 300 comprises a adhesive layer 350', a attachment area 330', and a second attachment area 331. The adhesive layer 350' does not extend to the edges of the carrier 300 in the vertical axis, and extends beyond an attached infusion pump 120. In another embodiment, the adhesive layer 350' is larger than the adhesive layer described hereinabove. The attachment area 330' extends beyond the carrier frame 310 towards the edge of the attachment area 330'. Additionally, the attachment area 330' may be larger than the attachment area 330 described hereinabove. The carrier 300 is attached to the adhesive layer 350' by the attachment area 330' and the second attachment area 331. For example, when the infusion pump 120 is attached to the carrier 300, the adhesive layer 350' is visible to the user. Additional embodiments, comprise a gripping member (not shown) disposed on the corner of the adhesive layer 350' that allows for removal of the carrier 300 from the body of the user.

Further embodiments of the carrier 300 are depicted in FIGS. 7, 8, and 9. In one embodiment (FIG. 7), the carrier 300 comprises a connection bar 332 that connects the attachment area 330 to the carrier frame 310. In another embodiment, the connection bar 332 is made of the same material as the carrier frame 310. In other embodiments (FIGS. 8 and 9), the carrier frame 310 comprises four cut-offs 320, and an attachment area 330 disposed at a central point of the carrier frame 310.

FIGS. 10, 11, 12 and 13 depict embodiments of the carrier 300 that are attached to the skin of a user in a vertical position. As described hereinabove, the carrier frame 310 is attached to the adhesive layer 350 at an attachment area 330 such that infusion pump 120 can be oriented in a manner suitable for the user.

Figure 14:
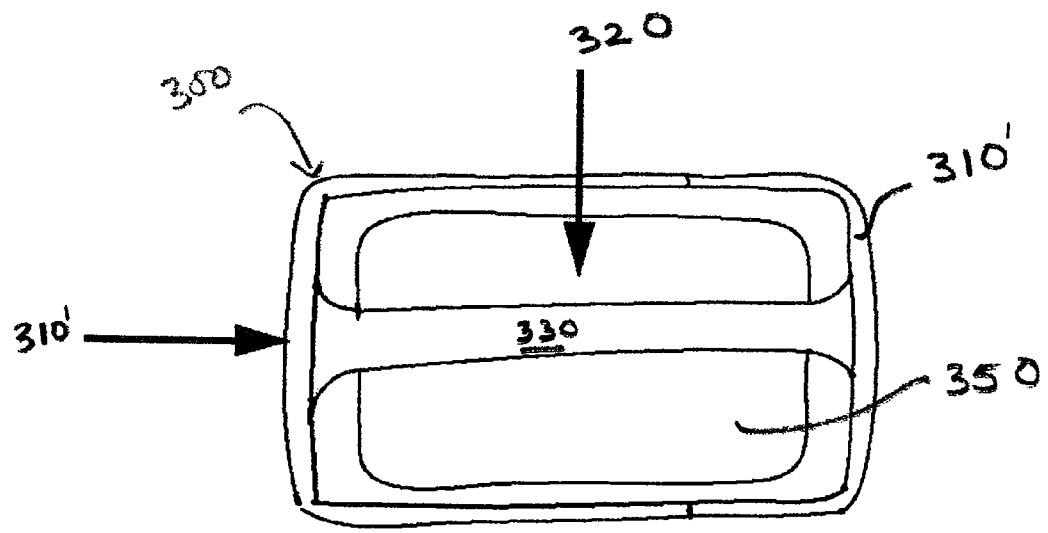
FIG. 14 depicts a top plan view of a carrier frame with one transversal connection bar and two cut-offs according to one or more of the embodiments shown and described herein.
Figure 15:
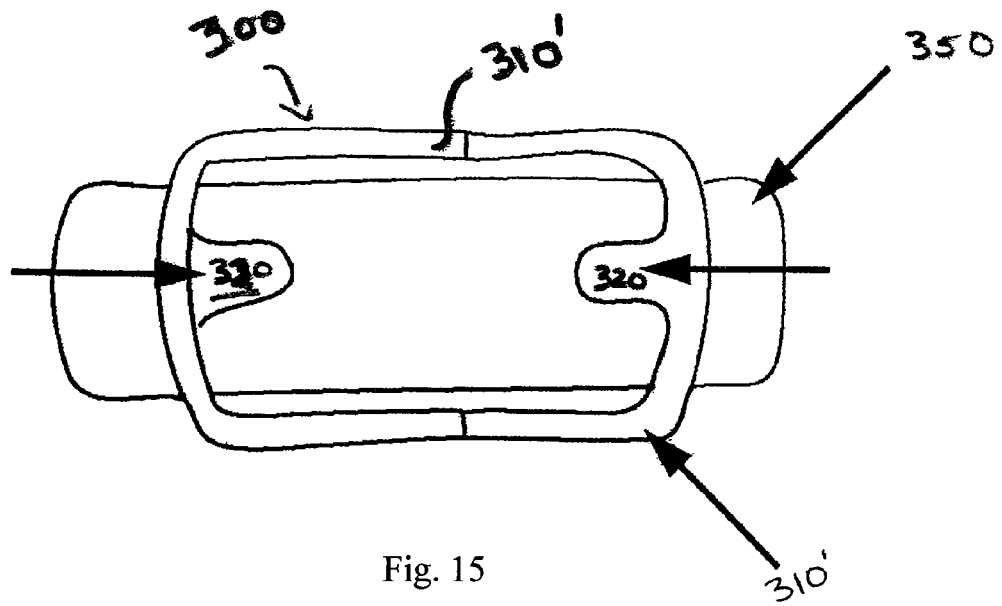
FIG. 15 depicts a top plan view of a carrier with double fixation and one cut-off according to one or more of the embodiments shown and described herein.

Referring now to FIGS. 14 and 15, embodiments of the carrier 300 comprise a carrier frame 310' having the same size as the infusion pump housing 210.

A carrier with a frame structure and cut-offs provides access to the pressure sensitive adhesive. The pressure sensitive adhesive can be pressed on by fingers after application and can be visually controlled by the patient. In addition, the pressure sensitive adhesive is accessible for pain free removal. Furthermore, skin respiration is provided for the portion of skin that is covered by the pressure sensitive adhesive by the space between the base surface of the device and the pressure sensitive adhesive. The air circulation inhibits skin irritation. Additionally, the frame structure of the carrier makes the carrier more elastic and flexible. The flexible structure results in wearing comfort because human skin is flexible.

Embodiments of the infusion pump housing 210 are depicted in FIGS. 16-19. The infusion pump housing 210 comprises a linear guide 400. The linear guide 400 is complimentary in shape to the guiding member 340, and mates with the guiding member 340 to attach the infusion pump 120 to the carrier. Embodiments of the linear guide 400 may comprise concave or convex shape. Additionally, the linear guide can extend the entire length of the infusion pump housing 210 or can partially extend along the length of the infusion pump housing 210.

Figure 20:
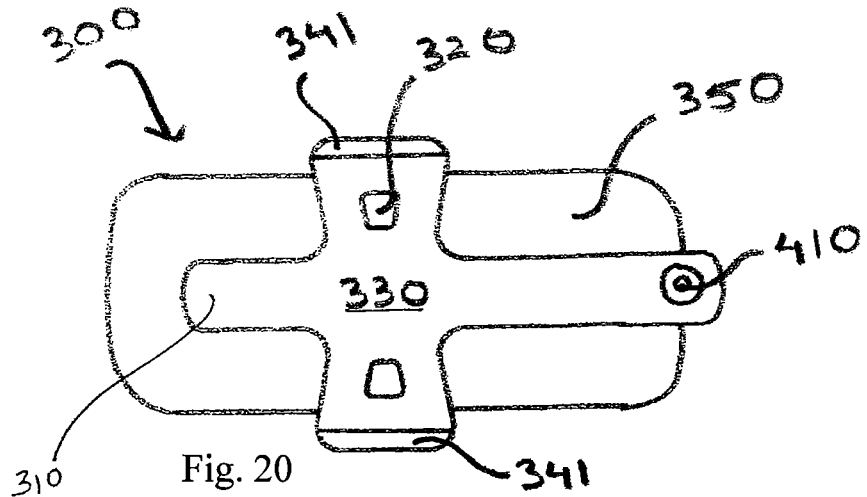
FIG. 20 depicts a top view of a carrier with a cross bar frame and a fastening means according to one or more of the embodiments shown and described herein.
Figure 21:
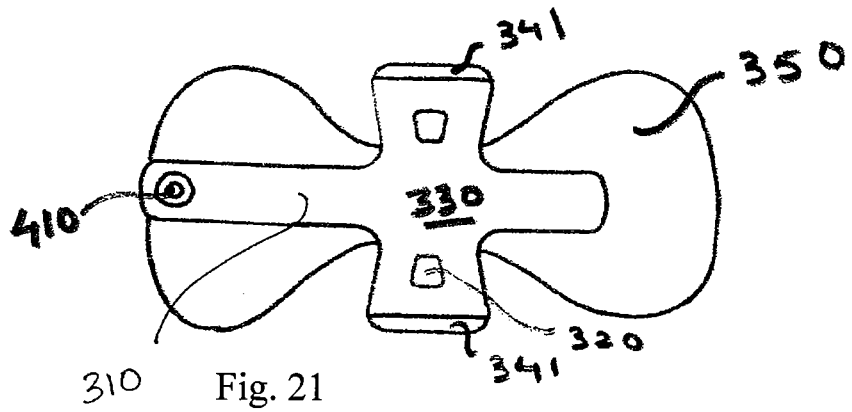
FIG. 21 depicts a top view of a carrier with a cross bar frame and a fastening means according to one or more of the embodiments shown and described herein.
Figure 22:
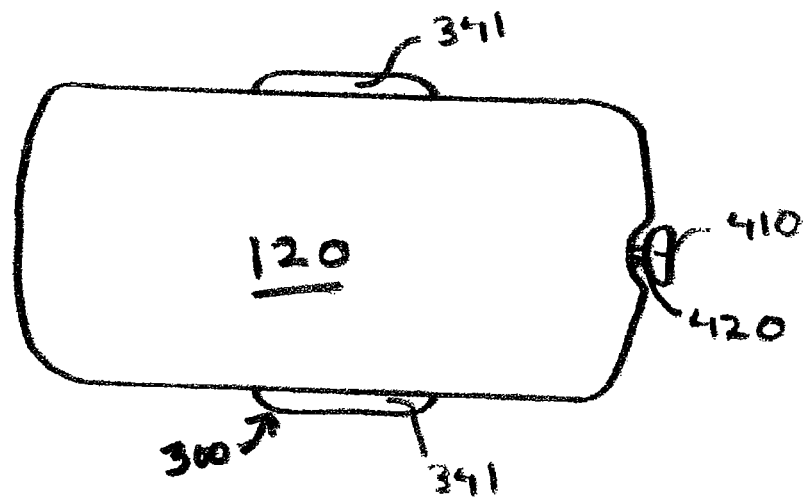
FIG. 22 depicts a top plan view of the attached infusion pump to the carrier of FIG. 20 according to one or more of the embodiments shown and described herein.
Figure 23:
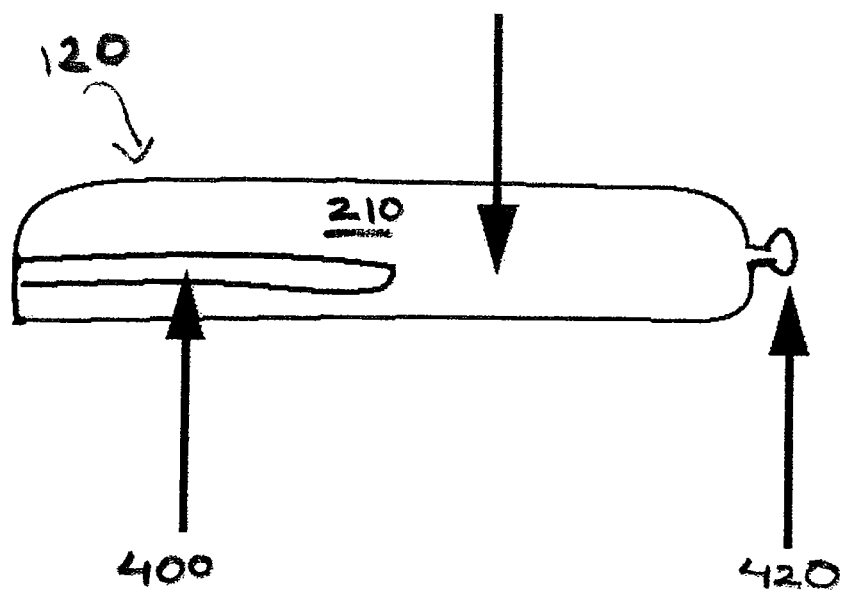
FIG. 23 depicts a side view of a drug delivery device with a snap fastener according to one or more of the embodiments shown and described herein.
Figure 24:
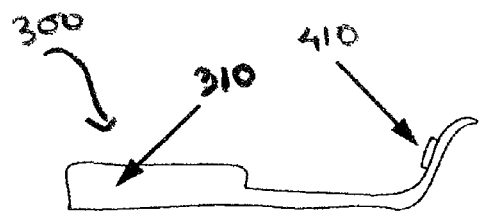
FIG. 24 depicts a side view of a carrier frame with a snap fastener according to one or more of the embodiments shown and described herein.
Figure 25:
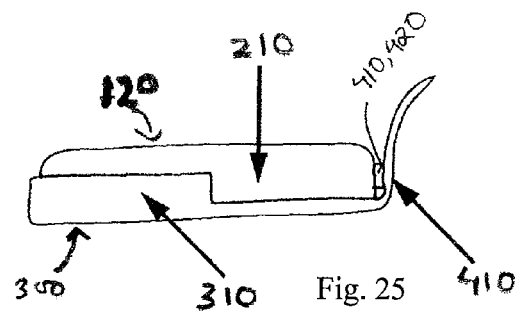
FIG. 25 depicts a side view of a carrier frame with a snapped drug delivery device according to one or more of the embodiments shown and described herein.
Figure 26:
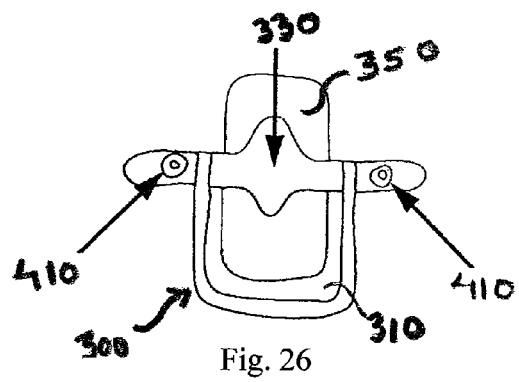
FIG. 26 depicts a top plan view of a carrier with two snap fasteners in the middle according to one or more of the embodiments shown and described herein.
Figure 27:
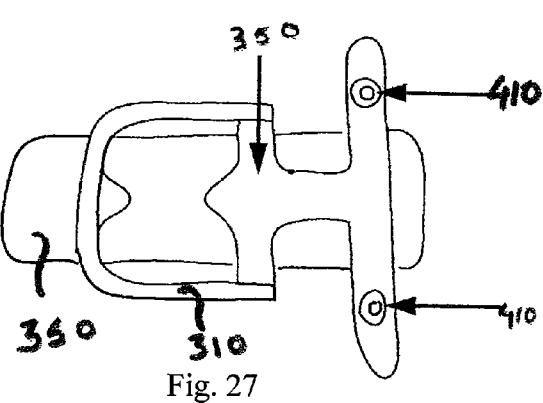
FIG. 27 depicts a top plan view of a carrier with two snap fasteners at the end according to one or more of the embodiments shown and described herein.
Figure 28:
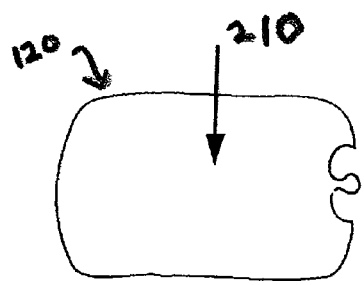
FIG. 28 depicts a top plan view of a drug delivery device with a snap fastener according to one or more of the embodiments shown and described herein.
Figure 29:
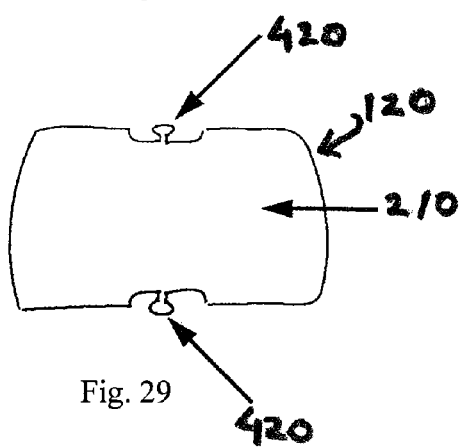
FIG. 29 depicts a top plan view of a drug delivery device with two snap fasteners according to one or more of the embodiments shown and described herein.
Figure 30:
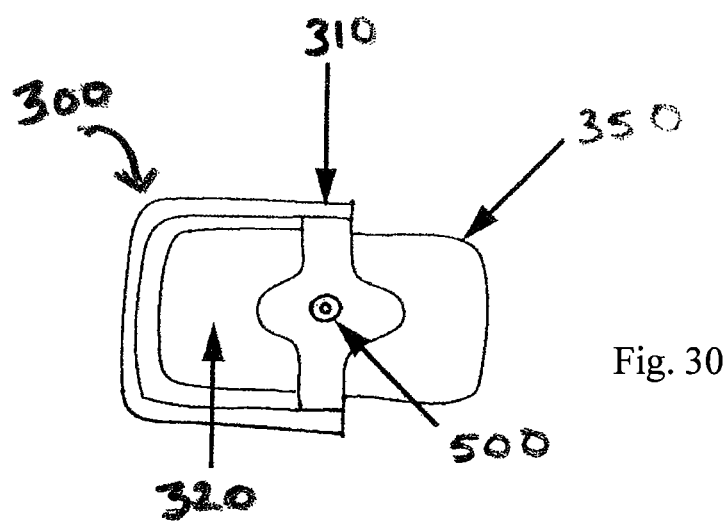
FIG. 30 depicts a top plan view of a carrier with infusion needle according to one or more of the embodiments shown and described herein.
Figure 31:
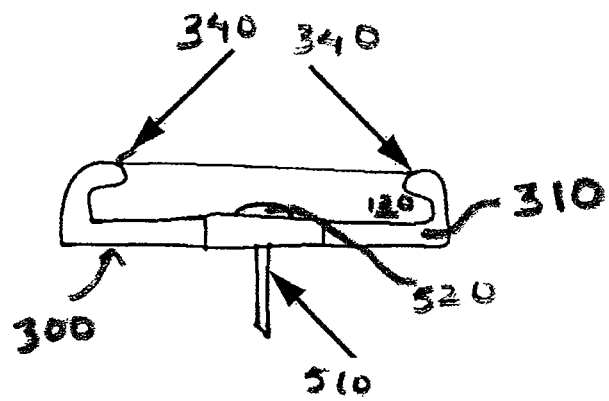
FIG. 31 depicts a side view of a carrier with linear guiding and infusion needle according to one or more of the embodiments shown and described herein.
Figure 32:
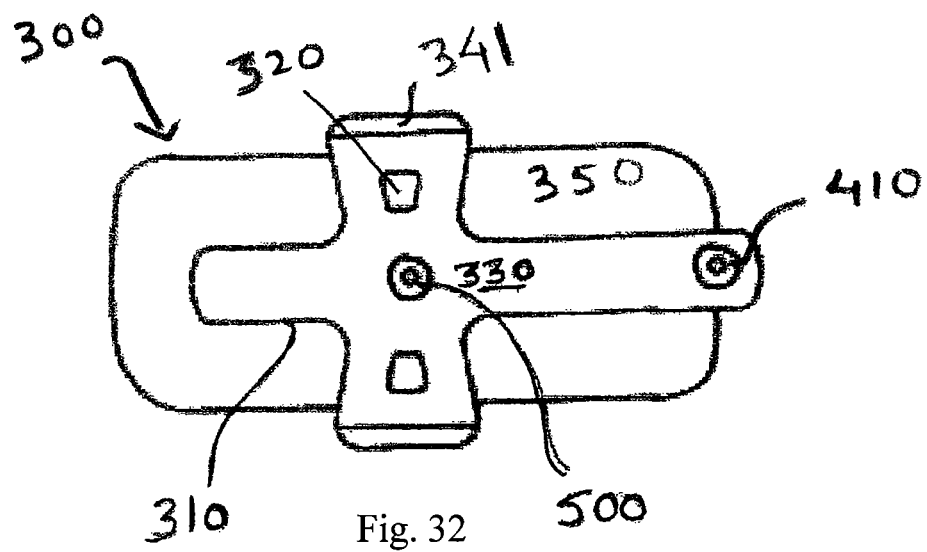
FIG. 32 depicts a top plan view of a carrier with an integrated needle according to one or more of the embodiments shown and described herein.

Embodiments of the carrier 300 are depicted in FIGS. 20 and 21. The carrier 300 is substantially cross shaped and comprises a relatively small carrier frame 310 with an attachment area 330. The carrier frame 310 comprises two cut-offs 320 near the attachment area 330. The attachment area 330 attaches the carrier frame 310 to the adhesive layer 350 along a central line along the horizontal axis. In further embodiments, the carrier 300 comprises a complementary ramp 341 that mates with the linear guide 400 of the infusion pump 120. For example, after the infusion pump 120 is attached to the carrier 300, the combination is small, discreet and moves about the horizontal axis.

Referring now to FIGS. 20-29, embodiments of the present disclosure comprise a carrier 300 comprising at least one fastening member 410, and an infusion pump comprising a corresponding member 420. The fastening member 410 can be any traditional fastening mechanism such as, for example, a snap fastener similar to textile snap fastener. The infusion pump 120 is securely attached to the carrier 300 via the fastening member 410 and corresponding member 420. For example, the fastening member 410 of the carrier 300 is mated with the corresponding member 420 of the infusion pump 120.

As depicted in FIGS. 1 and 30-32, embodiments of the carrier 300 comprise an integrated needle 500 comprising a cannula 510 and a septum 520. The integrated needle 500 is positioned near the center of the carrier 300, and delivers fluid into the body of the user. The cannula 510 inserts into the skin of the user. The septum 520 is disposed on the carrier 300, and hermetically seals the cannula 510 from the outside. In one embodiment, the infusion pump 120 comprises a connecting needle (not shown) that is to the fluid storing member 140. When the infusion pump 120 is connected to the carrier 300 the connecting needle pierces the septum 520 of the carrier 300 making a fluidic connection between the fluid storing member 140 and the cannula 510. It is noted that the infusion pump 120 and the carrier 300 can be separated and connected repeatedly. Each time the connection is established, the connecting needle pierces the septum 520. Additionally, the septum hermetically seals the cannula 510 from the outside when the connecting needle is withdrawn from the septum upon release of the connection between the carrier 300 and the body of the user. The cannula 510 can be made of steel or a more flexible material. In another embodiment, the cannula 510 is flexible. The cannula 510 is introduced into the tissue by means of a puncture needle. For example, the puncture needle and cannula 510 pierce the tissue together. After the introduction of the cannula, the puncture needle is removed leaving the cannula 510 in the tissue. In further embodiments, the carrier 300 comprises two sealing elements, such as an additional septum.

As depicted in FIGS. 1-22 and described above, a carrier 300 allows attachment of an infusion pump 120 to the human skin for an extended period of time through an adhesive layer 350. The infusion pump can easily be joined and separated from the carrier 300. This allows the infusion pump to be operated (e.g. to change the insulin reservoir) without detaching the skin-contacting surface of the medication delivery system from the skin.

Embodiments of the present disclosure allow the skin to move freely resulting in wearing comfort. Furthermore a fastening system situated at the side of the device allows to design thin delivery systems.

Figure 33:
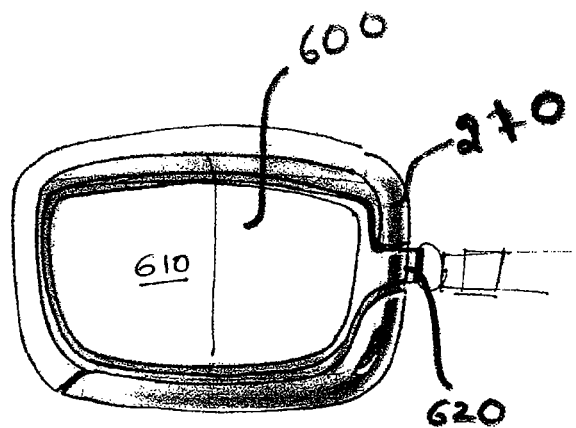
FIG. 33 depicts a top view of a carrier with a connector according to one or more of the embodiments shown and described herein.
Figure 34:
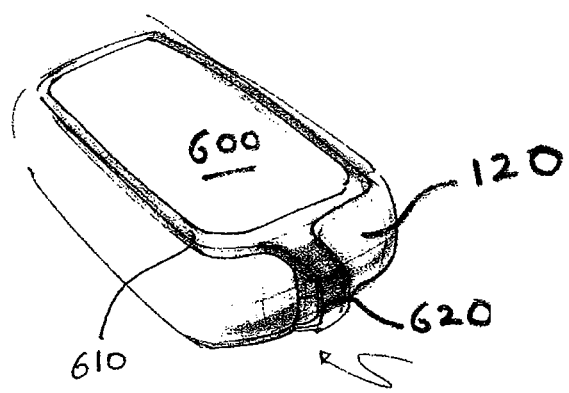
FIG. 34 depicts a top view of a carrier with a hook on connector according to one or more of the embodiments shown and described herein.

In further embodiments of the present disclosure, depicted in FIGS. 33 and 34, a carrier 600 comprises a carrier frame 610. The carrier frame 610 comprises a connector 620 at one end of the carrier frame 610. The carrier 600 mates with the infusion pump housing 210, and the user carries the infusion pump 120 in the carrier 600. In some embodiments, the connector 620 is attached to a clip or a key ring. Alternatively, the connector 620 is attached to a pouch such that it can hang from the person's neck. In one embodiment, the carrier 600 comprises a rigid material such as, for example, plastic. Alternatively, the carrier 600 may also comprise a semi rigid material or a soft material such as a fabric. In another embodiment the carrier frame 610 is smaller than the infusion pump housing 210. The carrier frame 610 attaches to the infusion pump housing 210 in a hook like manner. The carrier 600 may also comprise a connector 620 such that the infusion pump 120 may be carried in different ways by the user.

Embodiments of a carrier 700 are depicted in FIGS. 35 and 36. that can be attached to a wrist band is generally shown. The carrier 700 comprises a carrier frame 710 having a ramp 720 disposed on the interior of the carrier frame 710. The ramp 720 snap fits an infusion pump 120 into the carrier frame 710. The carrier frame 710 also comprises connecting tabs 730 disposed on opposite ends of the carrier frame 710. The connecting tabs 730 attach a flexible wrist band 750 to the carrier 700. For example, the infusion pump 120 is connected to the carrier 700 and carried around like a watch. Although a flexible wrist band 750 is depicted in the drawings, it is noted that the carrier 700 can be attached to a belt, a waist band, or a band that can be tied in the legs.

Figure 37:
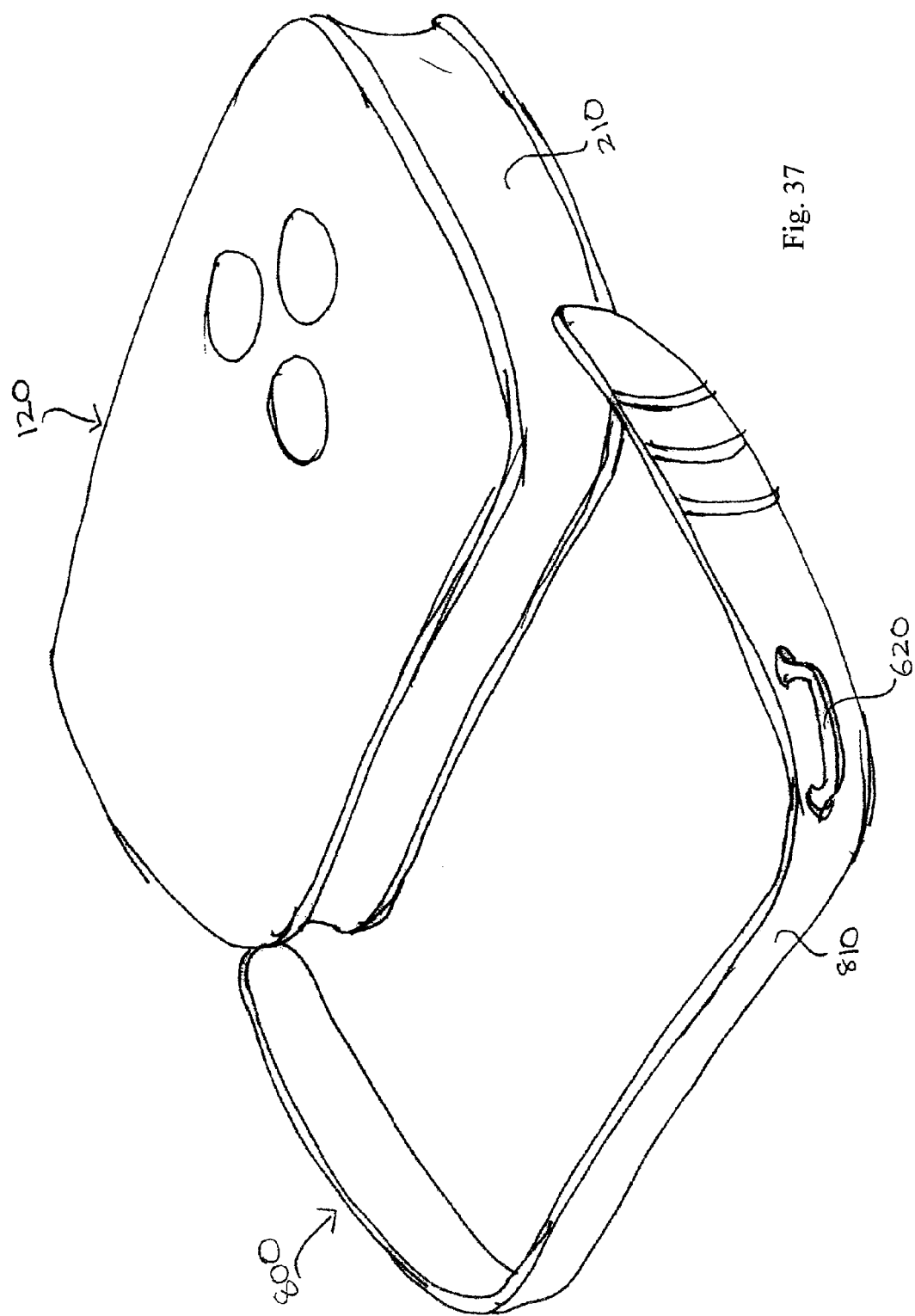
FIG. 37 depicts a perspective view of a carrier attached to the infusion pump as a side clip on according to one or more of the embodiments shown and described herein.

Referring now to FIG. 37, an embodiment of the carrier 800 is depicted. The carrier 800 comprises a carrier frame 810 that attaches to an infusion pump housing 210 by clipping around the infusion pump housing 210. In another embodiment, the carrier frame 810 comprises a connector 620.

Further embodiments of the present disclosure are depicted in FIGS. 38-41. Embodiments of a carrier 900 comprise a flat surface 910 and a perpendicular surface 920. The flat surface 910 is substantially perpendicular to the perpendicular surface 920 such that carrier 900 clips-on and attaches to one of the sides of the infusion pump housing 210. In another embodiment, the carrier 900 comprises cut-outs 930 such that operational buttons can be accessed by the user.

Figure 42:
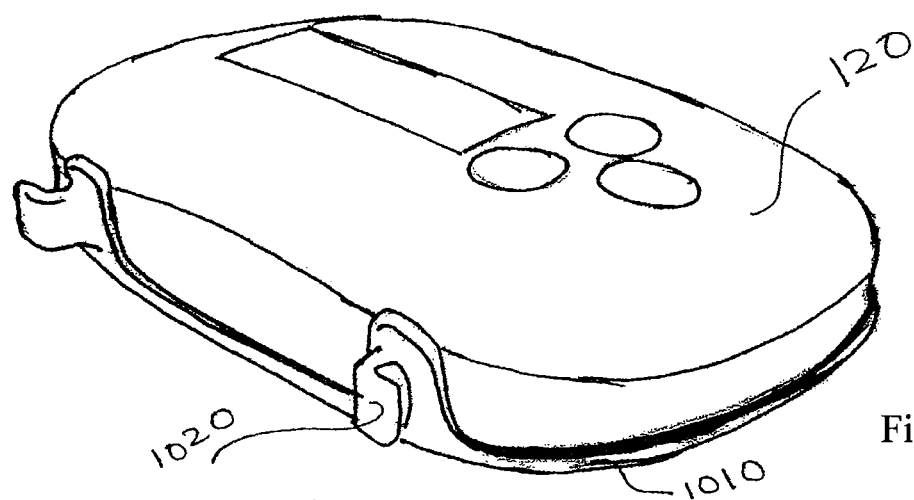
FIG. 42 depicts a perspective view of a carrier with hooks according to one or more of the embodiments shown and described herein.
Figure 43:
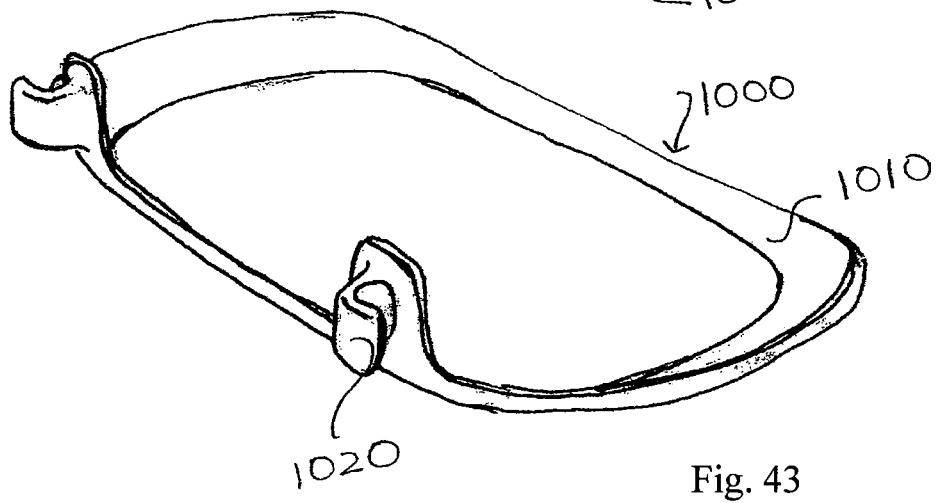
FIG. 43 depicts a perspective view of an infusion pump as attached to the carrier of FIG. 39 according to one or more of the embodiments shown and described herein.

Still further embodiments of the present disclosure are depicted in FIGS. 42 and 43. The carrier 1000 comprises a carrier frame 1010 that has the same shape as the infusion pump 120. Additional embodiments of the carrier frame 1010 comprise at least one hook 1020 that is integral with the carrier frame 1010. In another embodiment, the hook 1020 is a clip. Thus, the hook 1020 can be clipped to any part of the clothing such as, for example, a belt or a women's undergarment.

Skilled artisans appreciate that elements in the figures are illustrated for simplicity and clarity and have not necessarily been drawn to scale. For example, the dimensions of some of the elements in the figure may be exaggerated relative to other elements to help improve understanding of the embodiment(s) of the present disclosure.

The description of the embodiments provided herein is merely exemplary in nature and is in no way intended to limit the present disclosure or its application or uses.

It is noted that terms like "preferably", "commonly", and "typically" are not utilized herein to limit the scope of the claimed embodiments or to imply that certain features are critical, essential, or even important to the structure or function of the claimed invention. Rather, these terms are merely intended to highlight alternative or additional features that may or may not be utilized in a particular embodiment of the present disclosure.

For the purposes of describing and defining the present disclosure it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having provided the present disclosure in detail and by reference to specific embodiments thereof, it will be apparent that modification and variations are possible without departing from the scope of the present disclosure defined in the appended claims. More specifically, although some aspects of the present disclosure are identified herein as preferred or particularly advantageous, it is contemplated that the present disclosure is not necessarily limited to these preferred aspects.

What is claimed is:

1. An infusion system for holding an infusion pump and a fluid storing member connected to an infusion set through a tube on a body of a user, the system comprising:
   a carrier comprising a carrier frame, wherein the carrier frame comprises an adhesive layer and at least one cut-off, wherein the adhesive layer is accessible to the user through the at least one cut-off for pressing on by fingers after application and for being visually controlled by the user, wherein the carrier can be attached to and removed from the body of the user while leaving the infusion set in place on the body of the user;
   a guiding member disposed on the carrier frame; and
   an infusion pump housing comprising a linear guide configured to extend the full length of the infusion pump housing,
      wherein the infusion pump housing attaches to the carrier frame in an attaching direction via a linear sliding motion which mates the guiding member and the linear guide with each other and holds the infusion pump in place; and
      wherein the infusion pump housing has a substantially rectangular shape adapted to face outward from the user during use, and the linear guide comprises two convex shapes extending out on opposing sides of the infusion pump housing, each of the convex shapes being at the opposing side of the infusion pump housing located about 90 degrees from the substantially rectangular shape, and each linear guide being located equidistant from the substantially rectangular shape and an opposing side of the infusion pump housing adapted to face toward the user during use, and
      wherein the at least one cut-off comprises an opening within the carrier frame into which first and second attachment areas extend, and wherein each of the first and the second attachment areas extend centrally from opposing sides of the carrier frame and into the opening of the at least one cut-off, the first and the second attachment areas directly attaching the carrier to the adhesive layer and the first attachment area has a part extending beyond the carrier frame, away from the at least one cut-off and toward an edge of the adhesive layer.

2. The infusion system of claim 1, wherein a size of the adhesive layer is smaller than the carrier frame such that when the infusion pump is attached to the carrier the adhesive layer is not visible.

3. The infusion system of claim 1, wherein a size of the adhesive layer is larger than the carrier frame such that when the infusion pump is attached to the carrier the adhesive layer is visible.

4. The infusion system of claim 1, wherein the guiding member is concave in shape.

5. The infusion system of claim 1, wherein the carrier frame further comprises at least one fastening member to attach the infusion pump to the carrier.

6. The infusion system of claim 5, wherein the at least one fastening member is a snap fastener.

7. The infusion system of claim 1, wherein the carrier frame further comprises an integrated needle.

8. The infusion system of claim 1, wherein the carrier frame further comprises an integrated needle and a fastening member.

9. The infusion system of claim 1, wherein the carrier frame further comprises at least one connector.

10. The infusion system of claim 1, wherein the guiding member comprises a complementary ramp wherein the complementary ramp and the linear guide mate with each other to hold the infusion pump in place.

11. The infusion system of claim 1, wherein the guiding member comprises an indentation that secures the infusion pump to the carrier after the infusion pump is slid into the carrier.

12. The infusion system of claim 1, wherein the linear guide is complimentary in shape to the guiding member.

13. An infusion system for holding an infusion pump and a fluid storing member connected to an infusion set through a tube on a body of a user, the system comprising:
   a carrier comprising a carrier frame, wherein the carrier frame comprises an adhesive layer, a first attachment area and a second attachment area attached to the adhesive layer, and at least one cut-off wherein the adhesive layer is accessible to the user through the at least one cut-off for pressing on by fingers after application and for being visually controlled by the user, wherein the carrier can be attached to and removed from the body of the user while leaving the infusion set in place on the body of the user;
   an infusion pump housing comprising a second attaching means configured to extend the entire length of the infusion pump housing, the second attaching means being complimentary in shape to a first attaching means on the carrier frame,
      wherein the infusion pump housing attaches to the carrier frame in an attaching direction via a linear pushing motion which mates the first attaching means and the second attaching means with each other and holds the infusion pump in place; and
      wherein the infusion pump housing has a substantially rectangular shape adapted to face outward from the user during use, and the second attaching means comprises two convex shapes extending out on opposing sides of the infusion pump housing, each of the convex shapes being at the opposing side of the infusion pump housing located about 90 degrees from the substantially rectangular shape, and each of the convex shapes being located equidistant from the substantially rectangular shape and an opposing side of the infusion pump housing adapted to face toward the user during use, and
      wherein the at least one cut-off comprises an opening within the carrier frame into which the first and second attachment areas extend, and wherein each of the first and the second attachment areas extend centrally from opposing sides of the carrier frame and into the opening of the at least one cut-off, the first and the second attachment areas directly attaching the carrier to the adhesive layer and the first attachment area has a part extending beyond the carrier frame, away from the at least one cut-off and toward an edge of the adhesive layer.

14. A method of carrying an infusion pump and a fluid storing member connected to an infusion set through a tube on a human body of a user, the method comprising:

attaching the infusion set to the human body of the user;

providing a carrier having a carrier frame with a guiding member, wherein the carrier frame is configured to hold the infusion pump by bringing the carrier and the infusion pump into contact, wherein the carrier comprises an adhesive layer, a first attachment area and a second attachment area attached to the adhesive layer, and at least one cut-off wherein the adhesive layer is accessible to the user through the at least one cut-off; wherein the infusion pump has an infusion pump housing with a substantially rectangular shape adapted to face outward from the user during use, and a linear guide, the linear guide comprises two convex shapes extending out on opposing sides of the infusion pump housing, each of the convex shapes being at the opposing side of the infusion pump housing located about 90 degrees from the substantially rectangular shape, and each of the convex shapes being located equidistant from the substantially rectangular shape and an opposing side of the infusion pump housing adapted to face toward the user during use, and wherein the at least one cut-off comprises an opening within the carrier frame into which the first and second attachment areas extend, and wherein each of the first and the second attachment areas extend centrally from opposing sides of the carrier frame and into the opening of the at least one cut-off, the first and the second attachment areas directly attaching the carrier to the adhesive layer and the first attachment area has a part extending beyond the carrier frame, away from the at least one cut-off and toward an edge of the adhesive layer; and pressing the carrier frame comprising the adhesive layer and the first and second attachment areas through the at least one cut-off by fingers to attach the carrier to the human body, wherein the carrier after application can be removed from the human body while leaving the infusion set in place on the human body; and attaching the infusion pump housing to the carrier frame in an attaching direction via a linear pushing motion, wherein the infusion pump housing comprises the linear guide configured to extend the full length of the infusion pump housing, the linear guide being complimentary in shape to the guiding member, wherein attaching the infusion pump housing to the carrier frame mates the guiding member and the linear guide with each other and holds the infusion pump in place.

* * * * *